United States Patent [19]
Bechtold et al.

[11] Patent Number: 6,128,523
[45] Date of Patent: Oct. 3, 2000

[54] APPARATUS FOR FIXING THE FEMALE BREAST IN MEDICAL-TECHNICAL APPLICATIONS

[75] Inventors: Mario Bechtold, Röttenbach; Bernd Granz, Oberasbach; Hans-Peter Heindel, Fürth, all of Germany

[73] Assignee: Siemens Aktiengesellschaft, Munich, Germany

[21] Appl. No.: 09/179,354

[22] Filed: Oct. 14, 1998

[30]     Foreign Application Priority Data

Oct. 14, 1997  [DE]  Germany ................. 197 45 399

[51] Int. Cl.$^7$ .................................................. A61B 5/055
[52] U.S. Cl. ................................................ 600/411; 601/4
[58] Field of Search ................................. 600/410, 411, 600/415, 417, 421; 324/318, 312, 314, 306, 322; 601/4; 606/130

[56]                     References Cited

U.S. PATENT DOCUMENTS

| | | | |
|---|---|---|---|
| 3,226,976 | 1/1966 | Green . | |
| 5,437,280 | 8/1995 | Hussman | 128/653.2 |
| 5,534,778 | 7/1996 | Loos et al. | 324/318 |
| 5,681,327 | 10/1997 | Heywang-Koebrunner | 606/130 |
| 5,706,812 | 1/1998 | Strenk et al. | 128/653.5 |
| 5,897,345 | 4/1999 | Aida et al. | 600/411 |

FOREIGN PATENT DOCUMENTS

| | | |
|---|---|---|
| 26 33 828 | 2/1977 | Germany . |
| 44 42 609 C1 | 8/1996 | Germany . |

OTHER PUBLICATIONS

"Focused US System for MR Imaging–Guided Tumor Ablation" (Cline et al.), Magnetic Resonance Imaging, Mar. 1995, pp. 731–737.

"High–Intensity Focused Ultrasound in the Treatment of Prostatic Disease", (Foster et al.), Eur Urol, vol. 23, 1993, pp. 29–33.

*Primary Examiner*—Marvin M. Lateef
*Assistant Examiner*—Eleni Mantis Mercader
*Attorney, Agent, or Firm*—Herbert L. Lerner; Laurence A. Greenberg; Werner H. Stemer

[57]                     ABSTRACT

An apparatus for fixing a female breast for use in a variety of medical-technical applications such as, for example, ultrasound therapy, ultrasound diagnosis or biopsy. The fixing apparatus includes a container, into which the breast is introduced, a fixing diaphragm, and at least one compression cushion. The compression cushion presses the breast against the fixing diaphragm thereby achieving a fixed position of the breast.

12 Claims, 3 Drawing Sheets

APPARATUS FOR FIXING THE FEMALE BREAST IN MEDICAL-TECHNICAL APPLICATIONS

BACKGROUND OF THE INVENTION

Field of the Invention

The invention relates to an apparatus for fixing a position of a female breast for medical-technical applications.

In medical examination and treatment methods for the female breast, it is often important that the section of tissue under observation be exactly localized. This also applies for example to the thermotherapy method for diseased female breast tissue, which method is at present still in the development stage and would like to utilize the advantages of noninvasive treatment. In the method it is attempted to destroy for example cancerous tissue by High Intensity Focused Ultrasound (HIFU) or by the consequential heating of the tissue. This necessitates exact monitoring of the region of tissue undergoing therapy, which, at present, is usually effected by Magnetic Resonance (MR) systems. A handicap of ultrasound therapy is that the tissue to be given therapy must not move from the focus since otherwise inadequate heating of diseased tissue and/or destruction of healthy tissue might result. In ultrasound diagnosis, the breast is progressively irradiated with sound signals having a varying direction of propagation and focal plane. The associated echo responses obtained by contrast media are recorded and combined in a subsequent signal processing stage to give an overall image. Image data are thus recorded at different points in time and compared with one another. A change in the position of the region to be examined is undesirable in this case for the duration of examination. A further method for breast examination is biopsy (removal of tissue). In this case, it may be necessary to remove tissue from different regions of the breast, whose exact position must be known inter alia also with respect to one another. What is common to all the treatment and examination methods described is that they function even better and more reliably, the less the female breast changes its position in the course of the treatment and/or examination period. When a patient is in the prone position, the breast, without fixing, sinks for example by approximately 1 cm within 20 min.

The reference "Radiology", March 1995, pages 731 to 737, describes a configuration for ultrasound therapy of a female breast in which a sound transducer irradiates the breast of a patient who is in the prone position from bottom to top (perpendicular to the body plane of the patient). The sound transducer is located in a water-filled container sealed by a separating film. The patient lies directly on the separating film. In this case, the breast is compressed and fixed by the patient's weight and the geometry of the configuration. The article says nothing about the ultrasound coupling between the separating film and the breast. A coupling gel described for a comparable application of ultrasound therapy for the treatment of prostate complaints is described in the reference "Eur Urol", 1993, Vol. 23 (Supplement 1), pages 29 to 33, and is suitable for this purpose. Improved sound coupling to the surface of the skin is achieved, however, by a liquid. The gel coupling always holds the risk of air inclusions, in particular with such large coupling surfaces as the female breast, and of changes as a result of drying out in the case of relatively lengthy treatment periods. The method described for fixing the breast is additionally limited to the ultrasound therapy described in the article and cannot readily be transferred to other medical-technical applications.

An apparatus for fixing a female breast by two compensation (compression) plates having through holes for receiving a biopsy needle are provided at discrete points in the compensation plates is disclosed in German Patent DE 44 42 609 C1. The through holes are configured in the direction of the normal to the surface of the compensation plate in one compensation plate and inclined with respect to the surface normal in the other compensation plate. Since the through holes have a certain grid pattern, the apparatus enables the breast region to be captured only in a certain grid pattern, and not continuously. In order to achieve a larger capture range, the two compensation plates are additionally provided as access windows for the biopsy examination. If appropriate, it is also necessary to exchange the compensation plates during the examination. It is not possible to use the disclosed apparatus for a medical-technical application other than biopsy.

An apparatus for X-ray mammography is disclosed in Published, Non-Prosecuted German Patent Application DE 26 33 828 A1. In this case, the thorax is supported relative to a base by a pad. However, measures for genuine mechanical fixing of the female breast cannot be inferred.

SUMMARY OF THE INVENTION

It is accordingly an object of the invention to provide an apparatus for fixing the female breast in medical-technical applications which overcomes the above-mentioned disadvantages of the prior art devices of this general type, which is suitable for a variety of medical-technical examination or treatment methods for the breast and which permits the breast to be examined or treated in a wide region of the breast and in different ambient media, in particular in water and in air.

With the foregoing and other objects in view there is provided, in accordance with the invention, an apparatus for fixing a position of a breast of a patient having a predetermined body plane, including: a container having a container opening formed therein for receiving a breast;

a fixing diaphragm disposed in the container and configured as a sole access window for a variety of medical-technical applications, the sole access window covering a substantial region of the breast; and at least one compression cushion disposed opposite the fixing diagram for pressing the breast against the fixing diaphragm.

In accordance with an added feature of the invention, the at least one compression cushion includes a first, a second and a third compression cushion for fixing the breast by pressure in a direction within a plane that is parallel to a body plane of a patient and forming an angle of 70° to 110°, in particular 90°, to a direction of action between the fixing diaphragm and the first compression cushion.

In accordance with an additional feature of the invention, the at least one compression cushion includes a fourth compression cushion for fixing the breast by pressure in a direction forming a further angle of 70° to 110°, in particular 90°, to the body plane of the patient.

In order to fix the position of the female breast, use is made of an apparatus having the container for receiving the breast through the container opening, the fixing diaphragm and at least one compression cushion. The at least one compression cushion presses the breast against the fixing diaphragm, where the fixing diaphragm is constructed as the sole access window substantially covering the entire region of the breast for a variety of medical-technical applications.

The apparatus according to the invention can be used in a simple manner for breast fixing in a variety of medical examination and treatment methods, by utilizing the fixing diaphragm as the access window for the respective application. Even with only a single access window in the form of the fixing diaphragm, practically the complete region of the breast that is relevant for medical examination or treatment can be captured. Except for a small region of the breast located above the fixing diaphragm between the container opening and the patient's thorax, the complete breast can be reached through the fixing diaphragm acting as the access window. Otherwise the apparatus allows a highly flexible examination or treatment of the breast. Even during the application it is possible to vary the examination or treatment zone within the breast, even if this is associated with a direction change. Modification measures or renewed fixing of the breast are not necessary for this purpose. Furthermore, the choice of the container contents results in hat one is able at any time to react flexibly to the requirements regarding the ambient medium. Thus, in the case of ultrasound applications, the container can be filled with water, which is preferred for reasons of improved sound coupling, but the container may also be empty, that is to say filled with ambient air, if this is permissible, as, for example, in the case of biopsy.

Accordingly, further compression cushions are provided in one advantageous embodiment, with the result that the breast is fixed by pressure preferably also in the two orientations perpendicular to the direction of action between the fixing diaphragm and the first compression cushion. However, the advantageous effect is equally manifested if the directions differ by up to ±20° from the perpendicular orientations mentioned. In the plane running parallel to the body plane of the patient, the breast can advantageously be pressed against the container wall by a second compression cushion provided in accordance with the invention, and thus be fixed in this direction. As an alternative to the fixing on the container wall, a third compression cushion may preferably be provided, with the result that the breast can be fixed in a direction between the second and the third compression cushion. For the purpose of fixing in the orientation perpendicular to the body plane of the patient, a fourth compression cushion is advantageously fitted which presses the breast against the body plane. In a further advantageous refinement, it is possible to vary the size of at least one, in particular the first, of the four specified compression cushions, preferably with air or a liquid, in particular water. For the purpose of more flexible handling, the compression cushions may advantageously be configured such that they have a plurality of separately fillable chambers. Furthermore, the fixing diaphragm against which the breast is pressed by the first compression cushion may have a multi-part, domed and/or elastic construction for the purpose of improved adaptation to the anatomical nature of the breast. The advantageous refinements described enable flexible adaptation to the individual shape and size of the breast, thereby achieving optimum fixing in every case.

At least the surfaces of the compression cushions that come into contact with the skin are advantageously formed from latex. This achieves good skin compatibility of the compression cushions. Other skin-compatible materials are likewise possible.

In another advantageous embodiment, the apparatus for fixing the breast is used for ultrasound therapy and/or ultrasound diagnosis. In this case, an ultrasound device is located on that side of the fixing diaphragm which is remote from the breast. In this case, the device can be accommodated either in the same container or in a separate container. The fixing diaphragm then serves simultaneously as the sound access window to the breast. It must therefore be transparent to sound in this embodiment. This is preferably achieved by constructing it as a film, in particular as a perforated film, as a net or as a grid preferably made of the materials Mylar or nylon. In order to achieve good sound coupling, both the breast and at least parts of the ultrasound device (for example the ultrasonic transducer) are located in a liquid, preferably in water, which is, in particular, degassed and deionized. Even if the breast is pressed onto the fixing diaphragm to a great extent by the compression cushions and the liquid is thereby displaced to a very great extent, a thin film of liquid, which is desirable for good sound coupling, nevertheless always remains between the breast and the fixing diaphragm. For reasons of hygiene, it is advantageous to provide a liquid-impermeable partition between the fixing diaphragm and the ultrasound device, so that the liquid that comes into contact with the breast does not also come into contact with the ultrasound device. Since the ultrasound must also pass through the partition, the partition is preferably constructed as a film having a wall thickness of not more than 100 $\mu$m. Advantageous materials are Mylar or polyethylene. This ensures that the desired focusing of the ultrasound in the target region is not adversely affected. In order to be able to use the fixing device as flexibly as possible, it is advantageous if the medical-technical devices which are provided in accordance with the invention, thus including the ultrasound device, are located in a separate, second container. In the case of the ultrasound device, the second container is preferably connected to the first container via the liquid-impermeable partition and a seal. High system flexibility is achieved by this modularity.

The proportion of acoustic power that has been absorbed in the breast tissue to be treated is a matter of crucial importance in ultrasound therapy. Therefore, in an advantageous embodiment, at least one sensor for temperature detection and/or at least one sensor for the detection of sound intensity are provided in or on the compression cushions, preferably at least in or on the first compression cushion. The more sensors that are installed, the more accurately it is possible to draw conclusions about the absorbed acoustic power in the breast tissue from the measured values detected.

In a further advantageous refinement, a device for the removal of tissue (biopsy) is provided on that side of the fixing diaphragm that is remote from the breast. In exactly the same way as in the case of the ultrasound device described above, it is advantageous for the biopsy device, too, if it is located in a separate, second container which is connected to the first container. The comments regarding modularity and regarding system flexibility that have already been made above apply here, too. For removing tissue from the breast, it is not absolutely necessary to fill the first or the second container with a liquid. Rather, the application is preferably carried out in ambient air. If appropriate, however, it may be advantageous for reasons of protection against infection to fill at least the first container, in which the breast is situated, with an antibiotic solution. For biopsy applications, in an advantageous refinement, the fixing diaphragm is configured as a grid or, in particular, as an exchangeable film. The grid is advantageously composed of TPX, which has similar sound properties to water and, consequently, does not influence the sound passing through, or does so only to an insignificant extent. The same applies to the polyethylene film preferably provided in the film embodiment of the fixing diaphragm. A biopsy needle intended for the removal of tissue is inserted through the grid or the film and into the target region in the breast from which the tissue is to be removed. In the case of the advantageous film refinement of the fixing diaphragm, tissue removal points are marked by the holes in the film. This affords advantages during the subsequent assignment of tissue samples to the removal regions. The apparatus for fixing the breast can thus be used for entirely different medical-technical applications (ultrasound diagnosis and therapy, biopsy), it essentially being necessary only to adapt the fixing diaphragm to the specific application. The remaining parts of the apparatus for fixing the breast remain unchanged.

As an advantageous refinement, the fixing apparatus is provided as part of a larger MR installation. In the course of ultrasound therapy, which has already been discussed above, the temperature profiles in the treated tissue regions are preferably tracked by MR diagnosis. Therefore, in an advantageous refinement, one or more MR receiving antennas are provided in the fixing apparatus. The antennas can be fitted either in or on the compression cushions. They may alternatively be located on the container opening through which the breast is introduced into the container. The MR receiving antennas are preferably constructed as ring loops or as rod antennas. Other forms of antenna are likewise conceivable. The fixing apparatus according to the invention is also particularly well suited for use in MR installations because the fixing apparatus per se initially manages without metallic or current-carrying parts, which would otherwise lead to problems with the high electromagnetic fields of the MR installation (imaging artifacts, formation of current loops endangering patients). Specifically the compression cushions provided for fixing are extremely MR-compatible on account of their pneumatic or hydraulic volume regulating configurations. Other features which are considered as characteristic for the invention are set forth in the appended claims.

Although the invention is illustrated and described herein as embodied in an apparatus for fixing the female breast in medical-technical applications, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
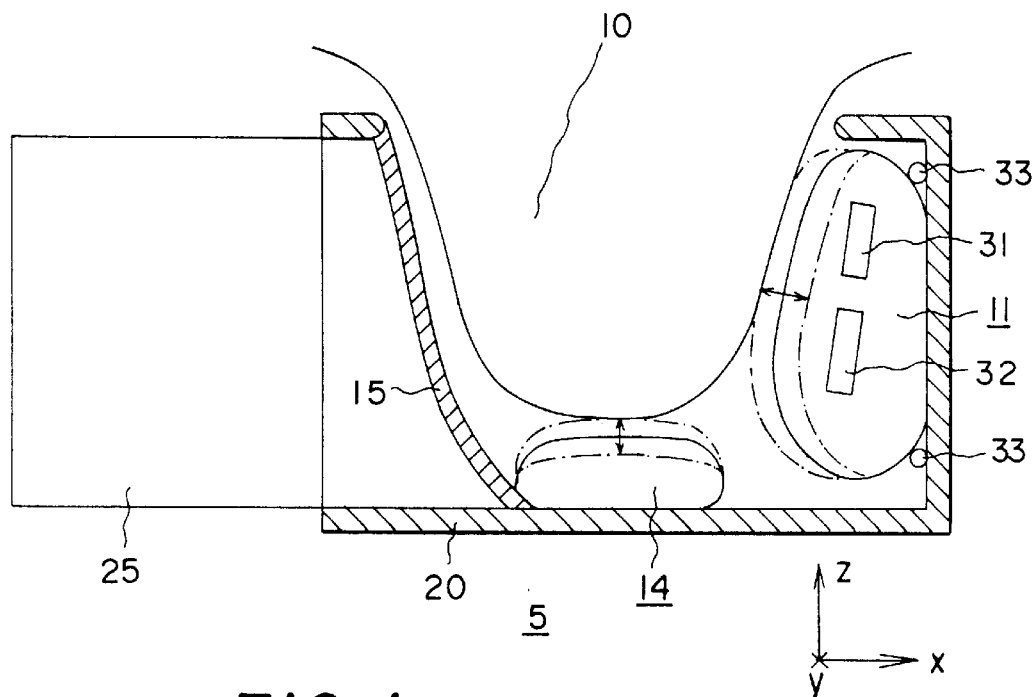
FIG. 1 is a diagrammatic, sectional view through a fixing apparatus for medical-technical applications according to the invention.
Figure 2:
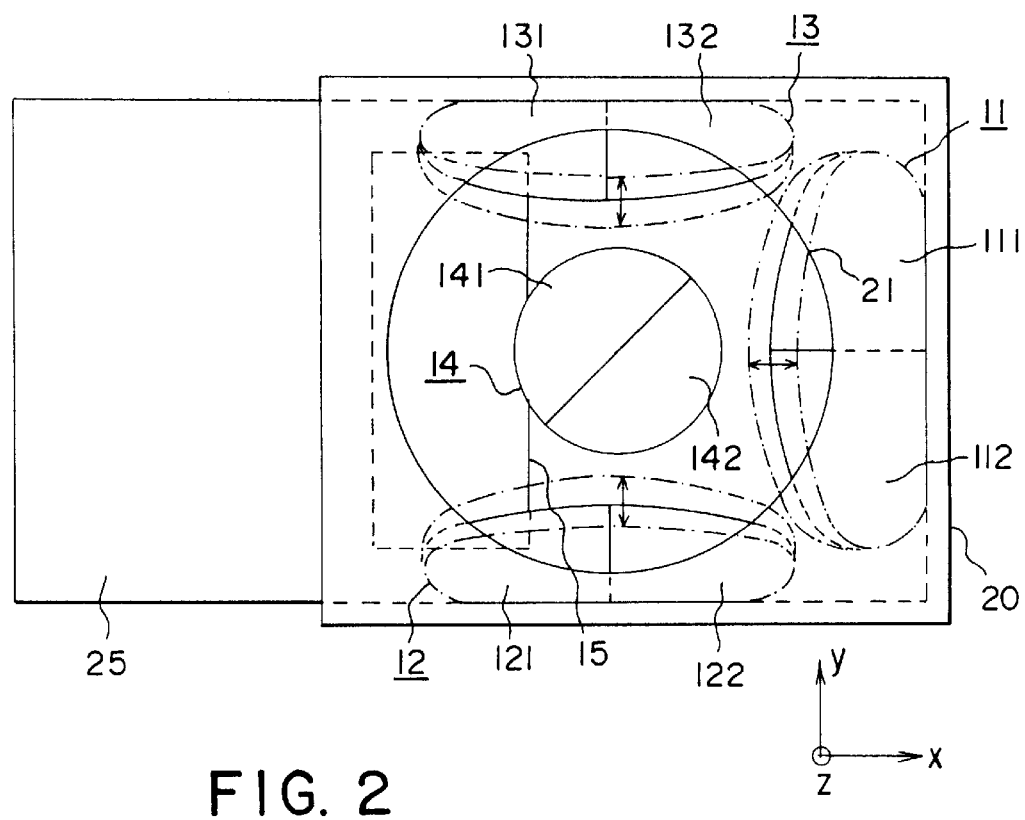
FIG. 2 is a plan view of a breast fixing apparatus for medical-technical applications.

In all the figures of the drawing, sub-features and integral parts which correspond to one another bear the same reference symbol in each case. Referring now to the figures of the drawing in detail and first, particularly, to FIG. 1 thereof, there is shown a central section through a fixing apparatus 5 for a female breast 10. FIG. 2 shows the same fixing apparatus 5 in a plan view. The fixing apparatus 5 includes a container 20 having a container opening 21, through which the breast 10 can be introduced into the container 20. In order to clarify the orientations, coordinate axes with auxiliary axes X, Y and Z are specified in each of FIGS. 1 to 4. In the illustration, a body plane of a patient lies approximately parallel to a plane spanned by the auxiliary axes X and Y. The breast 10 is pressed against a fixing diaphragm 15 by a first compression cushion 11 and, consequently, is fixed at least in the direction of the auxiliary axis X. In the direction of the auxiliary axis Y, the breast 10 is fixed by the pressure exerted on the breast 10 by a second compression cushion 12 and a third compression cushion 13. A fourth compression cushion 14 is provided for the purpose of fixing the breast 10 in the direction of the auxiliary axis Z. It exerts pressure on the breast 10 in the direction of the auxiliary axis Z. The breast 10 is fixed in all spatial directions by the compression cushions 11 to 14 and the fixing diaphragm 15 and, consequently, can no longer move in the course of an examination or treatment in accordance with a medical-technical device 25. The medical-technical device 25 is located on that side of the fixing diaphragm 15 which is remote from the breast 10. In this case, the fixing diaphragm 15 simultaneously serves as access window for the application of the medical-technical device 25. The compression cushions 11 to 14 are filled with water and their volume can be varied by varying the filling quantity. For more flexible adaptation to different breast sizes and shapes, the compression cushions 11 to 14 are provided with in each case two separately fillable chambers 111, 112, 121, 122, 131, 132, 141 and 142. If required by the anatomy of the breast 10, it is also possible to use compression cushions 11–14 having more than two chambers. In order to obtain maximum contact comfort, the compression cushions 11 to 14 are produced from a skin-compatible material, such as latex in the present exemplary embodiment. A temperature sensor 31 and a sound intensity sensor 32 are fitted in the compression cushion 11, in order to be able to acquire the measured variables of temperature and sound intensity which are important when the medical-technical device 25 includes an ultrasound application. With the aid of the two measured variables, it is possible to draw conclusions about the acoustic power absorbed in the breast 10 and about further derived variables such as, for example, the destruction of tissue.

In the event that the fixing apparatus 5 is intended to be used in connection with MR applications, an MR receiving antenna 33 in the form of a ring loop is fitted behind the compression cushion 11. The MR receiving antenna 33 detects MR signals that have been excited in the breast 10. What is of specific interest in this case is, for example, the temperature profile of a tissue region of the breast 10 undergoing therapy, which profile can be determined from the MR signals.

Figure 3:
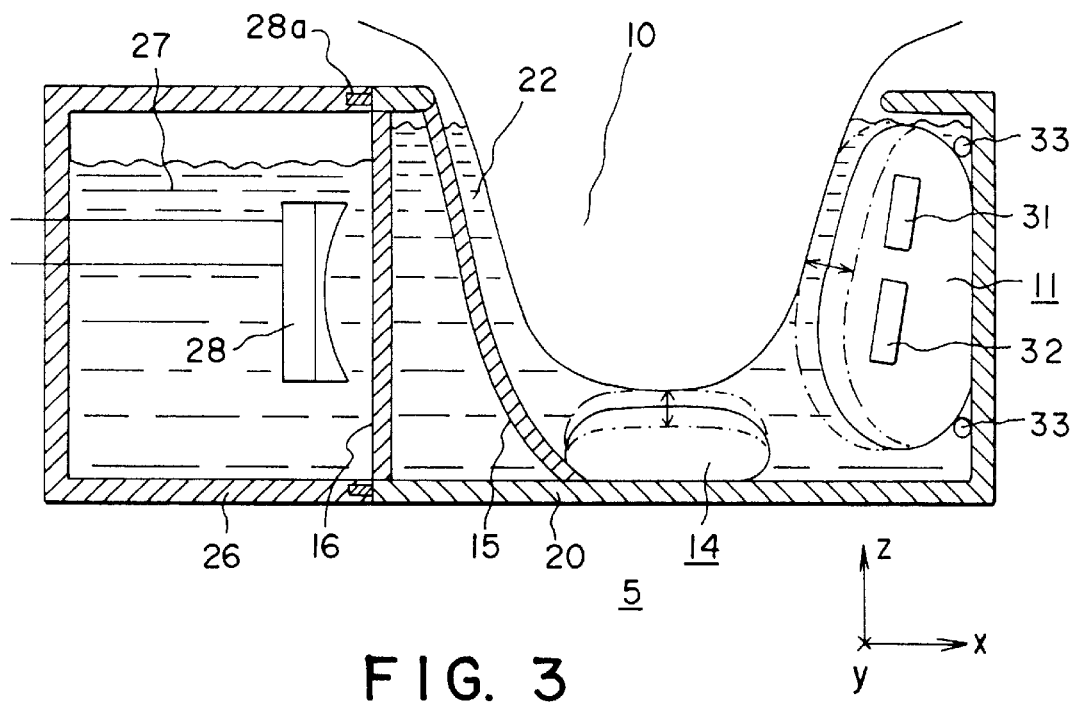
FIG. 3 is a sectional view through the breast fixing apparatus for ultrasound applications.

In FIG. 3, an ultrasound device 28 is provided as a configuration variant of the medical-technical device 25. The ultrasound device 28 may in this case be provided both for diagnostic and for therapeutic purposes. The ultrasound device 28 is located in a second container 26, which is connected to the first container 20 via a seal 28a and a partition 16. The partition 16 is impermeable to liquid and is produced from Mylar. In order to achieve improved sound coupling, the container 20 is filled with a liquid 22, with degassed and deionized water in the present case, and the container 26 is filled with a second liquid 27, likewise with degassed and deionized water. In this case, the liquid-impermeable partition 16 prevents the liquids 22 and 27 from mixing, which is desirable for reasons of hygiene. The partition 16 is composed of a Mylar film having a thickness of about 75 μm. In the ultrasound application, the fixing diaphragm 15 is configured as a perforated film likewise made of Mylar. Both the partition 16 and the fixing diaphragm 15 are sound-transmitting and do not influence the focusing of the ultrasonic beam.

Figure 4:
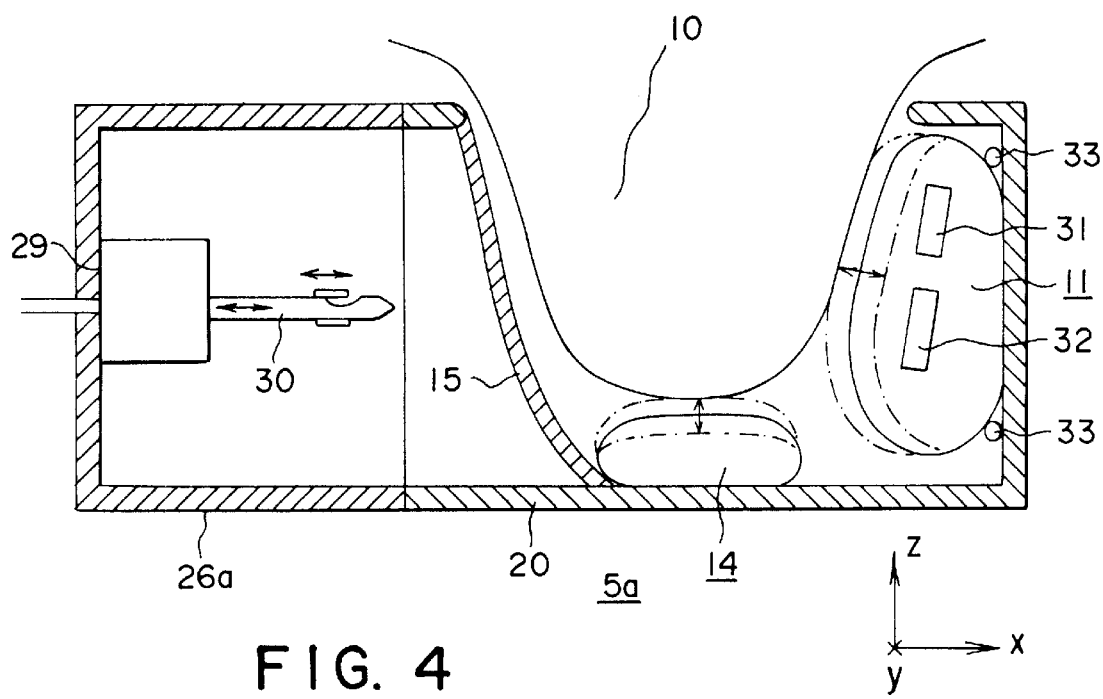
FIG. 4 is a sectional view through the fixing apparatus for a biopsy.

The embodiment of FIG. 4 provides a fixing apparatus 5a with a biopsy device 29. The biopsy device 29 is located in a separate, second container 26a, which is connected to the first container 20. Since, in the case of tissue removal, particular specifications are not normally imposed on the medium that surrounds the breast 10, air is situated in the container 20 and the second container 26a, but it may, if appropriate, be advantageous for reasons of protection against infection to fill at least the container 20 with an antibiotic solution. In the biopsy application, the fixing diaphragm 15 is configured as an exchangeable film made of polyethylene having a thickness of about 75 μm. For the purpose of removing tissue from the breast 10, a biopsy needle 30 is pushed through the film of the fixing diaphragm 15. In the process, the biopsy needle 30 leaves behind a permanent marking in the form of a hole in the fixing diaphragm 15, with reference to which marking the site of tissue removal in the breast 10 can still be determined even subsequently.

Figure 5:
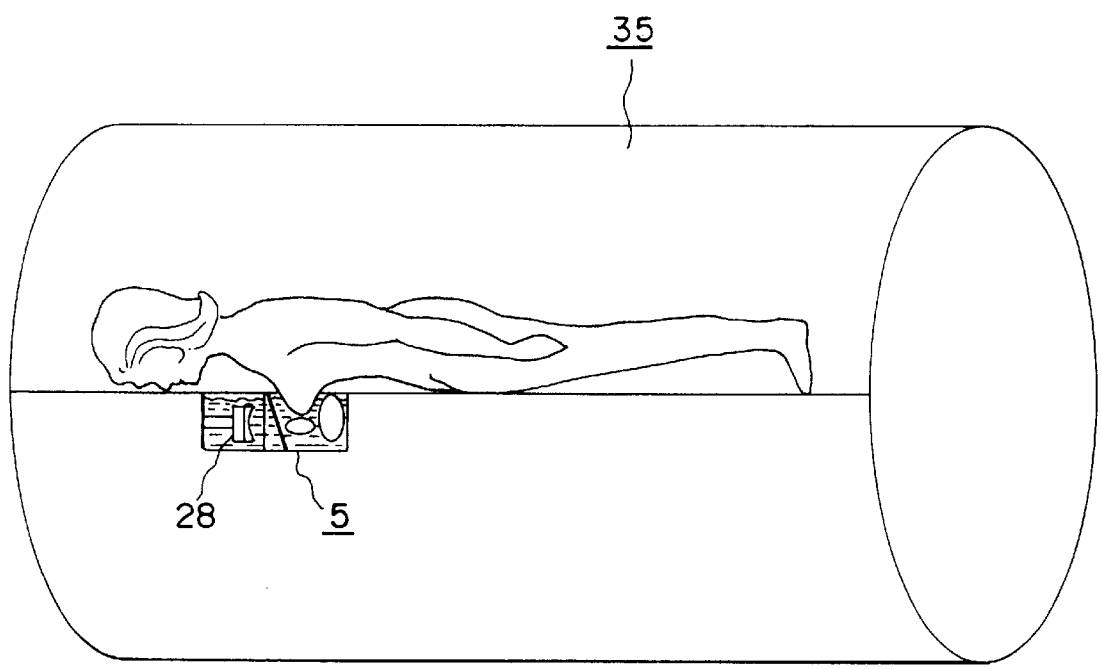
FIG. 5 is a diagrammatic view of the breast fixing apparatus as part of an MR installation.

In the exemplary embodiment of FIG. 5, the fixing apparatus 5, together with an ultrasound device 28, constitutes part of an MR installation 35. In the course of the ultrasound therapy (already discussed above) of diseased breast tissue, the MR diagnosis represents a preferred way of monitoring the temperatures in a treated tissue region.

In FIG. 5, the patient to be treated is shown in a horizontal position. The body position is not absolutely necessary, however, referring to the fixing apparatus 5. The fixing apparatus 5 can equally well be used when a patient is sitting or standing. What is critical in this case is the respective position of the fixing apparatus 5 referring to the body plane of the patient.

We claim:

1. An apparatus for fixing a position of a breast of a patient having a predetermined body plane, comprising:

a container having a container opening formed therein for receiving a breast;

a fixing diaphragm disposed in said container and being a sole access window for a variety of medical-technical applications, said sole access window covering a substantial region of the breast;

at least one compression cushion disposed opposite said fixing diagram for pressing the breast against said fixing diaphragm; and an ultrasound device disposed on a side of said fixing diagram remote from the breast for one of diagnosis and therapy of the breast, said ultrasound device irradiating the breast through said fixing diaphragm.

2. The apparatus according to claim 1, wherein said fixing diaphragm is made of a sound-transmitting film.

3. The apparatus according to claim 2, wherein said fixing diaphragm is made from a material selected from the group consisting of MYLAR and NYLON.

4. The apparatus according to claim 1, wherein said container is filled with a liquid.

5. The apparatus according to claim 4, wherein the liquid is water including a degassed and deionized water.

6. The apparatus according to claim 4, including at least one liquid-impermeable partition disposed between said fixing diaphragm and said ultrasound device.

7. The apparatus according to claim 6, wherein said at least one liquid-impermeable partition is made of a material selected from the group consisting of Mylar and polyethylene, and having a wall with a wall thickness not greater than 100 μm.

8. The apparatus according to claim 6, including a seal and a further container for housing said ultrasound device, said further container is at least partially filled with a further liquid and connected to said container via said at least one liquid-impermeable partition and said seal.

9. The apparatus according to claim 8, wherein the further liquid is water including a degassed and deionized water.

10. The apparatus according to claim 1, including at least one of a temperature sensor and a sound intensity sensor disposed in said at least one compression cushion.

11. The apparatus according to claim 1, including at least one of a temperature sensor and a sound intensity sensor disposed on said at least one compression cushion.

12. The apparatus according to claim 2, wherein said sound-transmitting film is selected from the group consisting of a perforated film, a sound-transmitting net, and a sound-transmitting grid.

* * * * *